(12) United States Patent
Minato et al.

(10) Patent No.: US 6,823,623 B2
(45) Date of Patent: Nov. 30, 2004

(54) METHOD OF CONTROLLING SEED DISEASE

(75) Inventors: Kanji Minato, Shiga (JP); Katsumi Shigeta, Shiga (JP)

(73) Assignee: Takii & Company, Limited, Kyoto (JP)

(*) Notice: Subject to any disclaimer, the term of this patent is extended or adjusted under 35 U.S.C. 154(b) by 62 days.

(21) Appl. No.: 09/885,829

(22) Filed: Jun. 20, 2001

(65) Prior Publication Data

US 2002/0023385 A1 Feb. 28, 2002

(30) Foreign Application Priority Data

Jun. 22, 2000 (JP) ........................................ 2000-187893

(51) Int. Cl.[7] .............................. A01C 1/06; A01C 21/00
(52) U.S. Cl. ............... 47/57.6; 47/DIG. 9; 47/DIG. 11; 47/58.1 SE; 504/100
(58) Field of Search ........................... 47/57.6, 58.1 R, 47/DIG. 9, DIG. 11; 71/5; 504/100

(56) References Cited

U.S. PATENT DOCUMENTS

| | | | |
|---|---|---|---|
| 4,229,442 A | | 10/1980 | Pinckard |
| 4,367,609 A | * | 1/1983 | Lloyd .......................... 47/57.6 |
| 4,668,512 A | | 5/1987 | Lewis et al. |
| 4,798,723 A | * | 1/1989 | Dart et al. ..................... 424/93 |
| 4,817,333 A | * | 4/1989 | Szepessy et al. ............... 47/58 |
| 4,828,999 A | * | 5/1989 | Jackson ....................... 435/235 |
| 5,113,619 A | * | 5/1992 | Leps et al. ................... 47/57.6 |
| 5,215,747 A | * | 6/1993 | Hairston et al. ............... 424/93 |
| 5,552,315 A | * | 9/1996 | Slininger et al. ......... 435/253.3 |
| 5,628,144 A | * | 5/1997 | Eastin ............................ 47/58 |
| 5,697,186 A | * | 12/1997 | Neyra et al. .................. 47/57.6 |
| 5,783,411 A | * | 7/1998 | Schisler et al. ................ 435/34 |
| 6,074,638 A | * | 6/2000 | Anderson et al. ......... 424/93.43 |

FOREIGN PATENT DOCUMENTS

| | | | | |
|---|---|---|---|---|
| JP | 05015384 | * | 7/1991 | ........... C12P/13/02 |
| JP | 5051305 | | 3/1993 | |
| JP | 05-227806 | | 9/1993 | |
| JP | 06-087716 | | 3/1994 | |

(List continued on next page.)

OTHER PUBLICATIONS

Control of Phytopathogenic Prokaryotes By Cutural Management and Chemicals, 16 pages, Apr. 2000.*
Seed Technology "Vegetable and Flower Seed Quality" A Symposium, Jun. 20, 1998, vol. 20, No. 2, pp. 198–209.
"Making Greater Use of Introduced Microorganisms for Biological Control of Plant Pathogens" R. James Cook, Annu. Rev. Phytopathol. 1993, 31:53–80.

(List continued on next page.)

*Primary Examiner*—Peter M. Poon
*Assistant Examiner*—Andrea M. Valenti
(74) *Attorney, Agent, or Firm*—Jordan and Hamburg LLP (57) ABSTRACT

For the purpose of obtaining disease-free seeds of high quality by efficiently controlling a seed borne disease of seeds of vegetable crops, ornamental plants and other herbage, seeds are subjected to a physical or chemical sterilization to reduce a fungal or bacterial amount held by the seeds and then the thus sterilized seeds are treated by an effective microorganism which is antagonistic against a pathogen of the seed borne disease. Controlling effect and fixing property of the effective microorganism can be enhanced by using a plurality of fungal or bacterial strains thereof. Examples of such effective microorganisms include fungi or bacteria belonging to the genus *Pantoea* or the genus *Leclercia* which is antagonistic against the pathogen belonging to the genus *Xanthomonas*.

14 Claims, 1 Drawing Sheet

FOREIGN PATENT DOCUMENTS

| | | | | |
|---|---|---|---|---|
| JP | 6253827 | 9/1994 | | |
| JP | 7025716 | 1/1995 | | |
| JP | 7075562 | 3/1995 | | |
| JP | 09124427 | 5/1997 | | |
| JP | 9224655 | 9/1997 | | |
| JP | 0203917 | 8/1998 | | |
| JP | 1004606 | 1/1999 | | |
| JP | 1253151 | 9/1999 | | |
| JP | 11-302120 | 11/1999 | | |
| SU | 1793878 | * 2/1993 | .......... | A01N/63/00 |
| WO | 85/01878 | 5/1985 | | |
| WO | WO 94/10845 | 5/1994 | | |
| WO | 97/02749 | 1/1997 | | |
| WO | 98/30077 | 7/1998 | | |

OTHER PUBLICATIONS

"Proceedings of the Workshop—Stand Establishment as Affected by Seed Quality, Water Relations, and Seed Treatment" Frederick J. Sundstrom et al., Hort Technology, vol. 2, No. 3, Jul.–Sep. 1992, pp. 345–349.

"Seedborne Diseases and Their Control" R. B. Maude, CAB International, 1996 (UK), pp. 173–178.

"Formulation of Microbial Biopesticides—Beneficial Microorganisms, Nematodes and Seed Treatments" H.D. Burges, Kluwer Academic Publishers, 1998 (The Netherlands), pp. 260–265, 282–283.

* cited by examiner

FIG. 1

METHOD OF CONTROLLING SEED DISEASE

BACKGROUND OF THE INVENTION

The present invention relates to a method of controlling diseases of seeds which have been infected with seed borne diseases.

Seeds for use in agricultural and horticultural production of, for example, vegetable crops, and ornamental plants, are produced in fields called as seed producing places, facilities such as green houses and plastic green houses. In these seed producing locations, seeds called as foundation seeds for use in producing seeds have been cultivated for seed production.

The seed production is to produce seeds for use in agriculture or horticulture from various kinds of foundation seeds. There is a case in which even when the thus produced seeds have a genotype to be targeted and sufficient germinating power, they are infected with diseases. Such diseases are called as seed borne diseases and are infected from mother plants which have been infected with diseases (Seeds Problems in Agriculture and Forestry, 161–183, Shun-ichiro Nakamura, Yokendo Ltd., 1985; Seed Quality Basic Mechanisms and Agricultural Implications, 160–171, Amarjit S Basra ed., Food Products Press, 1995). When seeds which have been infected with a seed borne disease are used for production of vegetable crops, not only an onset of the disease is exhibited from disease infected seeds, but also such seeds become an infectious source during a period of nursery or culturing to infect intrinsically disease-free seeds with disease whereupon production of vegetable crops is liable to be greatly damaged. Further, when a pathogen or a crop infected with a disease is left as remains in a soil of a field or in an installation of a green house or plastic green house, there are many cases in which onset of disease can be seen at the time of subsequent cultivation. Still further, more and more seeds of vegetables and seeds of ornamental plants have recently been exported. When seeds thereof are infected with a seed borne disease, they can not pass through quarantine so that they can not be exported or sold (Plant Pathogens and the World-Wide Movement of Seeds, Denis C. McGee, APS Press, 1997).

As described above, a loss in vegetable crops, seed sales or distribution business thereof which would be caused by the seed borne disease is extremely large so that it is a big problem to overcome such a disease in cultivation of seeds for seed production and seed sales (Ecology and Control of Seed Borne Diseases, Kan-ichi Ohata et al., Japan Plant Protection Assn., 1999; Seed Technology, Vol. 20, 2, 187–197, 1998).

A countermeasure which is taken at present is exemplified by sterilization of foundation seeds and sterilization of seeds obtained by seed production. The latter has widely been executed on a commercial basis. Included therein are, for example, soaking of seeds in an agrochemical solution, powder-coating or coating of seeds with an agrochemical, warm-water soaking of seeds, dry-heating treatment of seeds and other treatments (Seeds Problems in Agriculture and Forestry, 183–194, Shun-ichiro Nakamura, Yokendo Ltd., 1985). Although it is recognized that methods of such sterilizations are effective to some extent, sufficient sterilization effect can not always be obtained since sufficient sterilization will bring about reduction of germination rate of seeds and other problems.

Further, in recent years, a damage caused by the seed borne disease has rapidly been increased. It can not be denied that a reason thereof is attributable to the seed sterilization. This is because that, when the seeds are sterilized, not only pathogenic microorganisms but also ordinary microorganisms inhabiting on an outside surface of or inside the seed are reduced in number to a great extent whereupon a microbial air-pocket is generated in the seed, resulting in reducing a mutual suppression property in a biological field. Such reducing the mutual suppression property will permit survived pathogenic microorganisms even scarce in number to initiate infection thereby causing a severe onset of the disease. However, though the above-described features may be true, from the standpoint of controlling the seed borne disease, the seed sterilization can not all be excluded. This is because that the seed which is highly liable to be infected with pathogenic microorganisms has no other way to reduce a density of pathogenic microorganisms than by seed sterilization.

On the other hand, in recent years, in controlling plant diseases, apart from using synthetic agrochemicals, using effective microorganisms inhabiting in nature has been tried (New Strategy of Controlling Diseases, 141–188, Wataru Komada and Tadaoki Inaba et al., Zenkoku Nouson Kyouiku Kyoukai, 1992; Microorganism Technology for Protecting Agricultural Environment, Ienohikari Kyokai, 1998; Seed Technology, Vol. 20, 2, 198–208, 1998; Microbial Agrochemical, Masao Yamada et al., Zenkoku Nouson Kyouiku Kyoukai, 2000). The effective microorganisms to be utilized for such controlling diseases are those which are antagonistic against pathogens and suppress proliferation of the pathogens. Such effective microorganisms, being different from synthetic agrochemicals, proliferate on their own so that they hold a lasting controlling effect. Since they can suppress generation of agrochemical resistant microorganisms and inhibit in nature, they have an advantage in that there is almost no fear of causing an environmental pollution.

However, when the disease is viewed from a side of a disease controlling effect, it is a present state that there exists nearly no substance which exceeds agrochemicals. Reasons for it are generally summed up in two points as follows:

1. In a microbiological world abundant in diversity, microorganisms which are effective in suppressing only limited types of microorganisms, so-called pathogenic microorganisms are hardly fixed by being subjected to selection after treatment; and 2. Under a cultivation condition abundant in diversity, effective microorganisms are not always in an environment suitable for survival so that the controlling effect against pathogenic microorganisms can not always be consistently executed by a single-typed effective microorganisms. As a result, controlling effect to be aimed can not fully be obtained.

In order to overcome the above-described problems, efforts to generate an environment favorable for survival of the effective microorganisms have been executed. Namely, it is to find a method in which, when microorganisms are treated, materials called as a carrier (such as coral, peat moss, zeolite, vermiculite, perlite, and charcoal) or substrates as foods for effective microorganisms (such as rice husks, straws, paper pulp, crab shells, rice bran, and rape cakes) are added in order to provide effective microorganisms with a refuge that protects them from other ordinary microorganisms and changes of the environment whereupon the effective microorganisms stably survive (Control of Diseases by Antagonistic Microorganisms, 86–90, Toshio Kijima, Rural Culture Assn., 1992). As other methods, various proposals of soil treatments by effective microorganisms have been made (Japanese Patent Laid-Opens Nos. 56616/1994 and 106306/1999).

Further, a multiplicity of proposals have been made also in technologies of utilizing effective microorganisms for a purpose of controlling seed diseases (Japanese Patent Laid-Opens Nos. 51305/1993, 253827/1994, 25716/1995, 75562/1995, 224655/1997, 203917/1998, 4606/1999, and 253151/1999; U.S. Pat. No. 4,668,512; Annual Review of Phytopathology 31, 53–80, Cook, R. J., 1993; and Hort Technology, 345–349, 2(3), M. B. Bennett, V. A. Fritz, N. W. Callan, 1992).

However, there has not been developed a technology in which, in order to establish an environment favorable for survival of effective microorganisms in seeds, influence of ordinary microorganisms to the effective microorganisms is reduced and, at the same time, a contamination of seeds by pathogens is controlled to some extent by suppressing an amount of microorganisms inhabiting inside seeds by means of previously treating seeds by a physical or chemical technique and, thereafter, by treating the resultant seeds with effective microorganisms, particularly, a plurality of effective microorganisms, and, further, controlling of diseases are attempted to correspond to a change of cultivation environments.

Further, in International Patent Publication No. WO94/10845 (hereinafter referred to as WO94/10845), a synergistic microbicidal composition which comprises a strain belonging to the genus Pseudomonas as an effective microorganism and a specified agrochemical in combination have been proposed. However, in a case that treatments by the effective microorganism and the agrochemical are simultaneously performed as described above, the treatment methods of the effective microorganism and the agrochemical are same to each other whereupon respective optimal treatment methods by the effective microorganism and the agrochemical can not individually be selected from one another. Moreover, in such a simultaneous treatment, one of the agrochemical which gives no influence to the effective microorganism or the effective microorganism which has resistance to the agrochemical can only be utilized whereupon, even in WO94/10845, a combination which gives no influence to the effective microorganism by limiting types of effective microorganisms and agrochemicals has been selected.

SUMMARY OF THE INVENTION

The present invention has been attained under the above circumstances and has an object of providing a method of effectively controlling a seed borne disease from a seed of a vegetable and ornamental plant to obtain a desease-free seed of high quality.

As a result of an intensive study for overcoming the above-described problems, the present inventors have achieved the present invention by finding that, after a seed has been sterilized against a pathogenic microorganism which brings about a seed borne disease by a physical or chemical technique such as a dry-heating treatment and a treatment with a chemical substance, the seed is treated with an effective microorganism which is antagonistic against such a pathogenic microorganism thereby allowing to control a disease of the seed to be targeted.

That is, the method of controlling the seed disease of the present invention comprises the steps of: sterilizing the seed by a physical and/or chemical technique; and treating the seed with the effective microorganism which is antagonistic against such a pathogenic microorganism.

According to the method of controlling the seed disease, an infection by the pathogen of the seed borne disease can be suppressed to some extent by sterilizing the seed by at least one of physical and chemical techniques before treating it by the effective microorganism. Further, by suppressing an amount of the microorganism held by the seed by means of such sterilizing to some extent, an influence of an ordinary microorganism to the effective microorganism can be reduced thereby establishing an environment favorable for survival of the effective microorganism inside the seed. As a result, the effective microorganism which is provided to the seed after being sterilized can be fixed thereon without being selected thereby allowing to effectively exert a disease controlling effect.

Further, the method according to the present invention can select respective treatment methods of the effective microorganism and agrochemical separately different from the above-described simultaneous treatment method of the effective microorganism and agrochemical. Furthermore, according to the present-method, even when the seed has been sterilized by a chemical which has an influence to the effective microorganism, the influence of such a chemical to the effective microorganism can be suppressed as long as the chemical is provided to the seed by presoaking or other treatments. Therefore, the present method has a high degree of freedom in combination of physical or chemical technique for sterilization of the seed and the effective microorganism.

In the present invention, a so-called microbial air-pocket condition generated by the sterilization of the seed is avoided by actively contaminating the seed with the effective microorganism. On this occasion, even when a pathogenic microorganism exists in the seed to some extent after the seed has been subjected to sterilization, an establishment of an illustrative representation, namely, "infection readily goes to onset", can be avoided as long as the seed is contaminated again with the effective microorganism which has a higher potential than that of an infection source of the pathogenic microorganisms (biological remediation of a seed microorganism ecology system). As described above, the present invention provides a technique for controlling the seed borne disease by executing an effective microorganism treatment on a partially sterilized seed.

In the method of controlling the seed disease according to the present invention, it is preferable that the above-described effective microorganism comprises a plurality of microorganisms. Namely, it is advantageous that the seed which has been sterilized by the physical or chemical technique is treated with at least two types of strains of effective microorganisms. By treating the seed with a plurality of effective microorganisms, a controlling effect against a pathogen can be exerted in a consistent manner even under a variety of cultivating conditions.

DETAILED DESCRIPTION OF THE INVENTION

A preferred embodiment of a method of controlling a seed disease according to the present invention will hereafter be described in detail.

Figure 1:
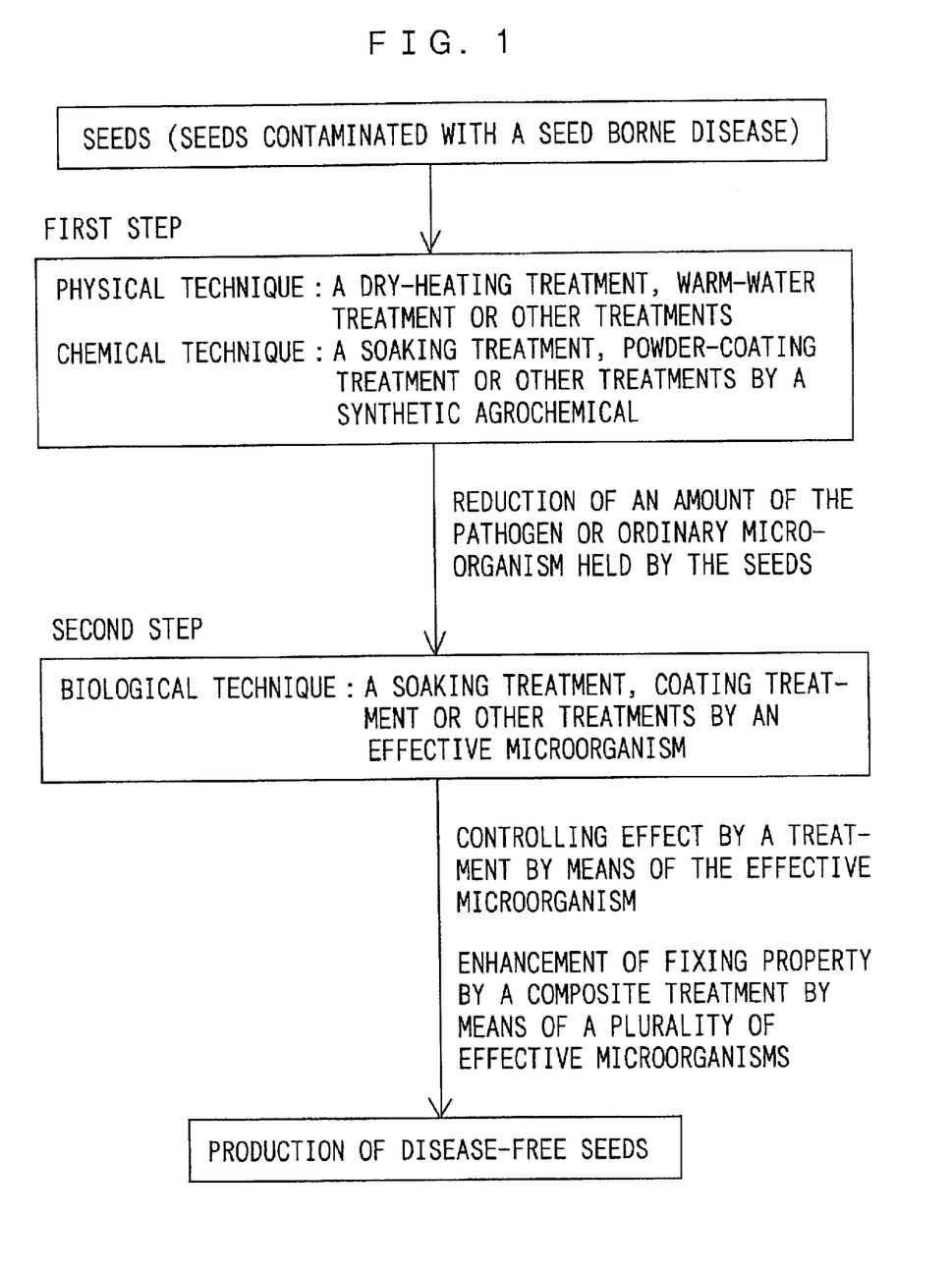
FIG. 1 schematically shows a method of controlling a seed disease according to the present invention.

As shown in FIG. 1, controlling the seed disease according to the present invention is performed in two steps. In a first step, a seed sterilization is performed by a physical or chemical technique; and in a second step, a treatment by an effective microorganism as a biological technique is performed.

As the seed to be targeted for treatment, a disease contaminated seed which has previously been contaminated with a seed borne disease is used; however, a seed which has not been contaminated can also be used aiming for achieving a prevention of the seed borne disease appropriate for such non-contaminated seed.

A physical or chemical technique of a seed sterilization in the first step is not limited in any particular manner; however, as the physical technique, a dry-heating treatment or warm-water treatment is exemplified while, as the chemical technique, a soaking treatment, powder-coating treatment, and other coating treatments with a synthetic agrochemical are exemplified. It is necessary that these techniques have a sterilization effect to a pathogenic or ordinary microorganism as a target for controlling the seed disease, but it is not required that these techniques have a complete sterilization effect. On the contrary, it is rather required to process the seed under a condition which will not give a detrimental effect such as reducing a germination power on the seed, namely, under a condition which is not harmful to the seed. Further, when the seed is subjected to a powder-coating treatment with a synthetic agrochemical, it is necessary that an amount of the agrochemical to be used for such treatment is determined taking into full consideration an influence into the effective microorganism to subsequently process the seed with.

A specific treatment condition differs according to types of seeds or seed borne diseases or other conditions so that it is hard to be generalized; however, for example, in the above-described dry-heating treatment, a condition in which a treatment temperature is between 40° C. and 80° C. and a treatment period of time is between 24 hours and 120 hours can be widely applied. Further, in the above-described warm-water treatment, a condition in which a treatment temperature is between 45° C. and 60° C. and a treatment period of time is between 10 minutes and 60 minutes can be widely applied.

As long as a detrimental effect on a germination and subsequent growth of the seed is not recognized, the respective techniques described above may favorably be combined with each other; on this occasion, a combination of physical techniques with each other, a combination of chemical techniques with each other or a combination of the physical and chemical techniques may be permissible.

By the seed sterilization of such first step, a number of pathogens or ordinary microorganisms is reduced so that an environment favorable for survival of the effective microorganism is established in the seed.

Thereafter, a disease-free seed can be obtained by treating the seed which has been subjected to sterilization with the effective microorganism in a second step.

The effective microorganism is not limited in any particular type, as long as it has an antagonistic property against a pathogen which brings about the seed borne disease of vegetable crops or ornamental plants, exhibits a sterilization effect of the seed subjected to a seed treatment and suppresses the onset of the disease when a plant body is cultivated. For example, included in the effective microorganisms are filamentous fungi belonging to, for example, the genus *Trichoderma*, the genus *Gliocladium*, and the genus *Penicillium* and the like, bacteria belonging to, for example, the genus *Pseudomonas*, the genus *Bacillus*, the genus *Enterobacter*, the genus *Pantoea*, and the genus *Leclercia*. Particularly, the effective microorganism which have been separated from seeds obtained from vegetables and ornamental plants by seed production are preferable.

The effective microorganism which is antagonistic against a specified pathogenic microorganism of a seed borne disease can be obtained by the following method:

Filamentous fungi and bacteria (hereinafter referred to as "candidate microorganisms" in general) isolated from a seed or a soil is streaked on a same medium as that of the pathogenic microorganisms of the seed borne disease which is a target to be controlled in a dual or cross manner and are cultured for several days under a temperature suitable for growing the pathogenic microorganisms (dual culture). After the microorganism have been cultured, growth thereof are observed; then, the one which apparently controlled the growth of the pathogenic microorganisms by the candidate microorganism is selected as the effective microorganism which has an antagonistic property (Laboratory Guide for Plant Pathology and Microbiology, 459–474, Satoshi Wakimoto et al., Soft Science Inc., 1993).

A method of treating seeds with the effective microorganism is not particularly limited; however, for example, (1) a method of soaking the seeds in an aqueous dispersion of an effective microorganism (also referred to as effective microorganism solution); (2) a method of pelleting the seeds by a coating material containing the effective microorganism; (3) a method of film-coating the seeds by a coating solution containing the effective microorganism; and (4) a method of hydrating the seeds by allowing the seeds to contact a carrier such as an absorbing polymer impregnated with the aqueous dispersion of the effective microorganism are illustrated. These methods may appropriately be combined with each other or be performed in a plurality of times, as long as no detrimental effect is given to the seeds. More specifically, in the method described in the above (1), the seeds may be soaked in a diluted cultivating solution of the effective microorganism; in the method described in the above (2), when the seeds are subjected to a pelleting treatment by a known method (for example, Japanese Patent Laid-Open No. 207807/1993), the effective microorganism may be mixed to a coating material such as talc and other inorganic materials; in the method described in the above (3), when the seeds are subjected to a film-coating treatment by a known method (for example, Japanese Patent Laid-Open No. 146707/1999), the effective microorganism may be mixed to a coating solution; and in the method described in the above (4), when the seeds are subjected to a hydration treatment before sowing for a purpose of enhancing a germination thereof by a known method (for example, Japanese Patent Laid-Opens Nos. 140219/1997 and 220002/1997), the effective microorganism to be targeted may simultaneously be absorbed along with water. On this occasion, since the effective microorganism is proliferated and favorably attached on an outside surface of or inside the seed during such treatment, the method is effective.

In the second step, though the seed can be treated with one type of the effective microorganism, it is preferable that, for the purpose of enhancing a fixing rate of the effective microorganism on the seeds and exerting a controlling effect on a pathogen in a consistent manner even under a variety of cultivating conditions, the seeds are treated by a plurality of types of effective microorganisms having an antagonistic property against a pathogenic microorganism of a same seed borne disease. On this occasion, a plurality of effective microorganisms may either be of a same species to or of different species from each other or either be of a same genus to or different genus from each other, as long as they are of different strains from each other. However, from the standpoint of allowing some latitude in fixing the effective microorganism on the seed or in the soil, which is an important factor in controlling the disease by the effective microorganism, it is preferable that the seeds are treated by strains having different growing aptitudes from each other. Therefore, a plurality of microorganisms are preferably of different species and, further, of different genus from each other. On this occasion, in a composite treatment by such plurality of effective microorganisms, mixing ratios of such microorganisms are not particularly limited.

An amount of the effective microorganism to be used for treatment in the second step can not be generalized since it depends on types of vegetable crops, ornamental plants, seed borne diseases, effective microorganisms, treatment methods, environments of cultivating fields and the other conditions. Further, since a seed cultivation is performed under a natural environment, it is preferable to meet general circumstances by changing treatment methods or treatment amounts of the effective microorganism in accordance with changes of the environments such as weather, meteorological and other natural phenomena.

In the above-described treatment in the second step, since the effective microorganism is imparted to the seeds in the environment favorable for the survival of the effective microorganism which has been established in the first step, the thus imparted effective microorganism is fixed on the seeds without being selected by an ordinary microorganism. Particularly, fixing property of the effective microorganism is enhanced by the composite treatment by means of a plurality of microorganisms whereupon a consistent effect on controlling the disease can be obtained.

The effective microorganism imparted to the seeds in a manner as described above, being different from a synthetic agrochemical, has an advantage such that it is proliferated on its own to have a prolonged controlling effect. On this occasion, not only the seed is disease-free by virtue of the effective microorganism proliferated on the surface of or inside the seed, but also it is possible to control the onset of the disease during the period of growing time of vegetables and plants. Further, when the effective microorganism can be fixed in a seed production field or a soil for growing vegetables or ornamental plants, the seed borne disease can perpetually be controlled resulting in saving labor consumption in disease-controlling work.

Furthermore, in the method of controlling the disease according to the present invention, adopted is a two-step treatment in which the seed sterilization in the first step does not necessarily perform a complete control so that a detrimental effect such as lowering of the germination rate thereof can be reduced.

Seeds of the vegetable crops which the present invention can utilize are not particularly limited and examples thereof include those of edible vegetable crops such as onion, welsh onion, and other crops of the family Liliaceae, those of carrot, celery, Japanese honewort and other crops of the family Umbelliferae, those of cabbage, broccoli, Chinese cabbage, radish, turnip and other crops of the family Brassicaceae, those of lettuce, leaf lettuce, garland crysanthemum, edible burdock and other crops of the family Compositae, those of spinach, Swiss chard, beet and other crops of the family Chenopodiaceae, those of tomato, egg plant, sweet pepper, pepper, solanum torvum, solanum integrifolium, tobacco, and other crops of the family Solanaceae, cucumber, melon, water melon, pumpkin, gourd and other crops of the family Cucurbitaceae, sweet corn and other crops of the family Gramineae, pea, broad bean, kidney bean, soy bean of the family Leguminosae and those of ornamental plants such as pansy, petunia, sultan snapweed, Russell prairie gentian, dianthus, ornamental kale, stock, primrose, sun flower, common zinnia, marigold, aster, common snapdragon, cyclamen, garden verbena and other ornamental plants.

Further, the seed borne diseases are not particularly limited and examples thereof include *Alternaria Brassicae, Alternaria brassicicola, Peronospora brassicae, Pseudomonas syringae* p.v. *maculicola, Xanthomonas campestris* p.v. *campestris* and *Phoma lingam* of the cabbage, *Alternaria japonica, Alternaria brassicae, Fusarium oxysporum* f.sp. *raphani, Xanthomonas campestris* p.v. *campestris* of the radish, *Alternaria brassicae, Xanthomonas campestris* p.v. *campestris, Verticillium dahliae* of the Chinese cabbage, *Alternaria dauci, Alternaria radicina, Xanthomonas campestris* p.v. *carotae* of the carrot, *Septoria apii, Sclerotinia sclerotiorum, Pseudomonas syringae* p.v. *apii* of the celery, *Alternaria porri, Botrytis allii, Botrytis byssoidea, Fusarium oxysporum* f. sp. *cepae* and *Peronospora destructor* of the onion, *Peronospora farinosa, Fusarium oxysporum* f. sp. *spinaciae, Colletotrichum dematium* of the spinach, *Alternaria solani, Clavibacter michiganensis* subsp. *michiganensis, Xanthomonas campestris* p.v. *vesicatoria* of the tomato, *Alternaria solani, Phomopsis vexans* of the egg plant, *Alternaria cucumerina, Pseudomonas syringae* p.v. *lachrymans, Xanthomonas campestris* p.v. *cucurbitae* of the cucumber and other diseases. Examples of diseases of the ornamental plants include *Alternaria znniae, Xanthomonas campestris* p.v. *znniae* of the common zinnia, *Sclerotinia sclerotiorum, Alternaria helianti* of the sun flower, *Xanthomonas campestris* p.v. *campestris* of the ornamental kale and other diseases.

EXAMPLES

The present invention will more specifically be described below by illustrating examples. In the examples, techniques for controlling the seed borne diseases using bacteria belonging to the genus *Pantoea* and the genus *Leclercia* which are antagonistic against pathogenic bacterium of the seed borne diseases belonging to the genus *Xanthomonas* are explained; however, the present invention is by no means limited to any particular type by explaining such techniques. Screening and cultivation of the effective microorganism:

Seeds used in the examples are as follows:

Seeds of cabbage: No. 1, Soshu, Haru Hikari No. 7, Wakamine, Winner, and 1488 which are each available from Takii & Co., Ltd.;

Seeds of broccoli: Anfuri 747, and Doshiko which are each available from Takii & Co., Ltd.;

Seeds of cauliflower: Violet Queen, and Snow Mystic which are each available from Takii & Co., Ltd.;

Seeds of Chinese cabbage: Disease resistant 60 days available from Takii & Co., Ltd.;

Seeds of radish: Disease resistant Sofutori available from Takii & Co., Ltd.; and Seeds of turnip: Swan, and Disease resistant Hikari available from Takii & Co., Ltd.

Each type of the above-described seeds was shaken in a physiological saline solution (a distilled water solution containing 0.85 weight % of sodium chloride) having 2.5 times the weight of the seeds for 2.5 hours. Then, the solution was evenly streaked on an albumin-agar culture medium. In six days after streaking, a colony which has emerged was isolated and, then, streaked on a potato dextrose-broth-agar culture medium (available from Difco Laborarories, Mich., U.S.A.) in a cross application manner against *Xanthomonas campestris* p.v. campestris to be cultured at 25° C. In 3 days after being cultured, a bacterium which controls growth of such *Xanthomonas campestris* p.v. *campestris* was selected as an antagonistic bacterium. As a result, three bacterial strains under names of TK-12, TK-151, and TK-185 were obtained. Taxonomic properties of these three strains are shown below in Table 1.

TABLE 1

| Testing items | TK-12 | TK-151 | TK-185 |
|---|---|---|---|
| Morphologic features | Rod-shaped | Short rod-shaped | Short rod-shaped |
| Gram staining properties | – | – | – |
| Spore-forming properties | – | – | – |
| Motility | + | + | + |
| Attitude toward oxygen | Facultative anaerobic | Facultative anaerobic | Facultative anaerobic |
| Oxydase | – | – | – |
| Catalase | + | + | + |
| OF tests | F | F | F |
| Colors of colonies | NP | NP | Yellow-tint |
| Generation of gas from lactose | – | + | – |
| Ornithine decarboxylase | – | – | – |
| Arginine dihydrolase | – | – | – |
| Lysine decarboxylase | – | – | – |
| Urease | – | – | – |
| Generation of acids: | | | |
| L-arabitol | – | – | – |
| D-galacturonic acid | + | + | – |
| Potassium 5-ketogluconate | + | – | – |
| Lipase | – | – | – |
| Generation of acids: | | | |
| Sodium pyruvate | – | + | – |
| β-glucosidase | + | + | + |
| Generation of acids: | | | |
| D-mannitol | + | + | + |
| D-maltose | + | + | + |
| Generation of indole | – | + | – |
| N-acetyl-β-glucosaminidase | – | – | ± |
| β-galactosidase | + | + | + |
| Generation of acids: | | | |
| Glucose | + | + | + |
| sucrose | + | – | + |
| L-arabinose | + | + | + |
| D-arabitol | – | – | + |
| α-glucosidase | – | – | – |
| α-galactosidase | + | + | – |
| Generation of acids: | | | |
| Trehalose | + | + | + |
| L-rhamnose | + | + | + |
| Inositol | + | – | + |
| adonitol | – | – | – |
| palatinose | – | – | – |
| β-glucronidase | – | – | – |
| Generation of acids: | | | |
| D-cellobiose | + | + | – |
| D-sorbitol | + | – | – |
| α-maltosidase | – | – | – |
| Utilization of malonates | + | + | + |
| Allyl-L-aspartate amidase | – | – | – |

"NP" shows that no characteristic color has been generated in colonies; and
"±" shows that judgment is suspended.

From Table 1, the strains TK-12, and TK-185 have been identified as *Pantoea* sp. and the strain TK-151 as *Leclercia adecarboxylata*. These strains were named as *Pantoea* sp. TK-12, *Pantoea* sp. TK-185 (FERM BP-7618 (transferred from FERM P-17885 deposited on Jun. 5, 2000 to the deposit based on the Budapest Treaty on May 24, 2001)) and *Leclercia adecarboxylata* TK-151 (FERM BP-7617 (transferred from FERM P-17875 deposited on May 29, 2000 to the deposit based on the Budapest Treaty on May 24, 2001)) in the above-described sequence and the latter two were deposited with The International Patent Organism Depositary, National Institute of Advanced Industrial Science and Technology located at AIST Tsukuba Central 6, 1—1, Higashi 1-chome, Tsukuba-shi, Ibaraki-ken, 305-8566 Japan under the names described in respective brackets.

Example 1

Controlling *Xanthomonas campestris* p.v. *campestris* Against Seeds of Cabbage (1)

After seeds of cabbage (under the name of Shutoku available from Takii & Co., Ltd.) which were previously confirmed as being contaminated with *Xanthomonas campestris* p.v. *campestris* were subjected to a preliminary dry-heating treatment at 40° C. for 1 day and then sterilized by means of physical technique such that the seeds were subjected to a dry-heating treatment at 75° C. for 2 days. Subsequently, in Examples 1-1 to 1-3, after the seeds were soaked in a YPG liquid medium (also referred to as bacterial liquid) in which each of TK-12, TK-151 and TK-185 has been cultured for about 25 hours (and adjusted to have a bacterial concentration of about $3.0 \times 10^9$ cfu/g (wherein the cfu/g represents a number of colonies formed in 1 g of the bacterial liquid)) for 10 minutes, they were dried by blowing air at 35° C. for 18 hours. Further, in Example 1-4, after the seeds were soaked in a bacterial liquid containing an equal amount of each of the above-described three strains for 10 minutes, they were dried in a same manner as above. On this occasion, seeds which have been subjected to a dry-heating treatment at 75° C. for 2 days were named as Comparative Example 1-1; seed which have been subjected to a preliminary dry-heating treatment at 40° C. for one day were named as Comparative Example 1-2; and seeds which have not been subjected to any treatment were named as Comparative Example 1-3.

Seeds after having been subjected to respective treatments described above were shaken in a physiological saline solution (containing 0.85 wt % of sodium chloride therein) having 2.5 times the weight of seeds for 2.5 hours. Thereafter, the saline solution was streaked on each of mFS culture medium and mCS20ABN culture medium for *Xanthomonas campestris* p.v. *campestris* which are semi-selective media by an amount of 100 µl and incubated at 25° C. A number of colonies of *Xanthomonas campestris* p.v. *campestris* formed on each culture medium in 4 days was counted whereupon a degree of contamination against 1 g of seeds was determined. Further, 200 grains of seeds subjected to each treatment were investigated for the germination rates thereof. The result is shown in Table 2.

TABLE 2

| Examples | Treatments | Degrees of contamination by *Xanthomonas campestris* p.v. *campestris* (cfu/g) | Germination rates (%) |
|---|---|---|---|
| Example 1-1 | Dry-heating treatment at 75° C. for 2 days; Treated with TK-12 | $2.21 \times 10^2$ | 91.0 |

TABLE 2-continued

| Examples | Treatments | Degrees of contamination by Xanthomonas campestris p.v. campestris (cfu/g) | Germination rates (%) |
|---|---|---|---|
| Example 1-2 | Dry-heating treatment at 75° C. for 2 days; Treated with TK-151 | $8.94 \times 10^2$ | 92.5 |
| Example 1-3 | Dry-heating treatment at 75° C. for 2 days; Treated with TK-185 | $5.50 \times 10^2$ | 95.5 |
| Example 1-4 | Dry-heating treatment at 75° C. for 2 days, Treated with a composite of 3 bacterial strains | $1.63 \times 10^2$ | 93.0 |
| Comparative Example 1-1 | Dry-heating treatment at 75° C. for 2 days | $1.49 \times 10^4$ | 86.5 |
| Comparative Example 1-2 | Dry-heating treatment at 40° C. for 1 day | $1.44 \times 10^5$ | 84.0 |
| Comparative Example 1-3 | No treatment | $3.12 \times 10^5$ | 83.3 |

As shown in Table 2, Examples 1-1 to 1-4 which have been treated with antagonistic bacteria after subjected to a dry-heating treatment were lower in a contamination degree of *Xanthomonas campestris* p.v. *campestris* and higher in germination rates than Comparative Examples 1-1 and 1-2 which have been subjected only to a dry-heating treatment. Further, Example 1-4 in which seeds were treated with a composite of antagonistic bacteria was lower contamination degree than those treated with a single strain.

Example 2

Controlling *Xanthomonas campestris* p.v. *campestris* Against Seeds of Cabbages (2)

After seeds of cabbage (under the name of Soshu available from Takii & Co., Ltd.) which were previously confirmed as being contaminated with *Xanthomonas campestris* p.v. *campestris* were first soaked in a 500-time diluted solution of Chemiclon G (an agent of calcium hypochlorite available from Nippon Soda Co., Ltd.) for 10 minutes and then dried by blowing air at 35° C. for 18 hours whereby seeds were sterilized by a chemical technique. Subsequently, in Examples 2-1 to 2-3, after the seeds were soaked in a YPG liquid medium (also referred to as bacterial liquid) in which each of TK-12, TK-151 and TK-185 has been cultured for about 20 hours (and adjusted to have a bacterial concentration of about $2.0\times10^9$ cfu/g) for 10 minutes, they were dried by blowing air at 35° C. for 18 hours. Further, in Example 2-4, after the seeds were soaked in the bacterial liquid containing each of the above-described three strains in an equal amount to each other for 10 minutes, they were dried in a same manner as above. On this occasion, seeds which have been treated by the 500-time diluted solution of Chemiclon G but not treated by the antagonistic bacteria were used as Comparative Example 2-1; seed which have been treated by a 150-time diluted solution of Chemiclon G but not treated by the antagonistic bacteria were used as Comparative Example 2-2; seeds which have been treated by a 50-time diluted solution of Chemiclon G but not treated by the antagonistic bacteria were used as Comparative Example 2-3; and seeds which have not been treated were used as Comparative Example 2-4.

Seeds after having been subjected to respective treatments described above were shaken in a physiological saline solution (containing 0.85 wt % of sodium chloride therein) having 2.5 times the weight of seeds for 2.5 hours. Thereafter, the saline solution was streaked on each of mFS culture medium and mCS20ABN culture medium for *Xanthomonas campestris* p.v. *campestris* which are semi-selective media by an amount of 100 μl each and incubated at 25° C. A number of colonies of *Xanthomonas campestris* p.v. *campestris* formed on each culture medium in 4 days was counted whereupon a contamination degree against 1 g of seeds was determined. Further, 200 grains of seeds subjected to each treatment were investigated for the germination rates thereof. The result is shown in Table 3.

TABLE 3

| Examples | Treatments | Degrees of contamination by *Xanthomonas campestris* p.v. *campestris* (cfu/g) | Germination rates (%) |
|---|---|---|---|
| Example 2-1 | Treated by a 500-time diluted solution of Chemiclon G; Treated with TK-12 | $8.56 \times 10^2$ | 74.0 |
| Example 2-2 | Treated by a 500-time diluted solution of Chemiclon G; Treated with TK-151 | $1.88 \times 10^2$ | 75.5 |
| Example 2-3 | Treated by a 500-time diluted solution of Chemiclon G; Treated with TK-185 | $9.38 \times 10^2$ | 80.5 |
| Example 2-4 | Treated by a 500-time diluted solution of Chemiclon G; Treated with a composite of 3 bacterial strains | $2.06 \times 10^2$ | 82.5 |
| Comparative Example 2-1 | Treated by a 500-time diluted solution of Chemiclon G | $1.31 \times 10^4$ | 77.0 |
| Comparative Example 2-2 | Treated by a 150-time diluted solution of Chemiclon G | $2.44 \times 10^3$ | 75.0 |
| Comparative Example 2-3 | Treated by a 50-time diluted solution of Chemiclon G | $4.25 \times 10^2$ | 69.0 |
| Comparative Example 2-4 | No treatment | $2.06 \times 10^5$ | 83.5 |

As shown in Table 3, seeds in Examples 2-1 to 2-4 which have been treated with antagonistic bacteria after treated by a 500-time diluted solution of Chemiclon G were each reduced to a same level in a contamination degree of *Xanthomonas campestris* p.v. *campestris* as that of seeds treated by a 50-time diluted solution of Chemiclon G and, moreover, they were not reduced in germination rates to be caused by a damage from the agrochemical while it was observed that the seeds which have been treated by the 50-time diluted solution of Chemiclon G were reduced in such rates. From the above-described features, it was found that, according to the present invention, high effect in controlling disease can be obtained without bringing about a noxious microbial effect.

Example 3

Controlling *Xanthomonas campestris* p.v. *campestris* Against Seeds of Broccoli After seeds of broccoli (under the name of Haitsu available from Takii & Co., Ltd.) which were previously confirmed as being contaminated with *Xanthomonas campestris* p.v. *campestris* were first soaked in a 500-time diluted solution of Chemiclon G for 10 minutes and then dried by blowing air at 35° C. for 18 hours. Subsequently, in Examples 3-1 to 3-3, after the seeds were soaked in a YPG liquid medium (also referred to as bacterial liquid) in which each of TK-12, TK-151 and TK-185 has been cultured for about 20 hours (and adjusted to have a bacterial concentration of about $2.0 \times 10^9$ cfu/g) for 10 minutes, they were dried by blowing air at 35° C. for 18 hours. Further, in Example 3-4, after the seeds were soaked in the bacterial liquid containing each of the above-described three strains in an equal amount to each other for 10 minutes, they were dried in a same manner as above. On this occasion, seeds which have been treated by the 500-time diluted solution of Chemiclon G but not treated by the antagonistic bacteria were used as Comparative Example 3-1; seed which have been treated with a treating solution containing equal amounts of a 250-time diluted solution of Chemiclon G and a mixed bacterium solution of the above-described three strains were used as Comparative Example 3-2; and seeds which have not been treated were used as Comparative Example 3-3.

Seeds after having been subjected to respective treatments described above were shaken in a physiological saline solution (containing 0.85 wt % of sodium chloride therein) having 2.5 times the weight of seeds for 2.5 hours. Thereafter, the saline solution was streaked on each of mFS culture medium and mCS20ABN culture medium for *Xanthomonas campestris* p.v. *campestris* which are semi-selective media by an amount of 100 µl each and incubated at 25° C. A number of colonies of *Xanthomonas campestris* p.v. *campestris* formed on each culture medium in 6 days was counted whereupon a contamination degree against 1 g of seeds was determined. Further, 200 grains of seeds subjected to each treatment were investigated for the germination rates thereof. The result is shown in Table 4.

TABLE 4

| Examples | Treatments | Degrees of contamination by *Xanthomonas campestris* p.v. *campestris* (cfu/g) | Germination rates (%) |
|---|---|---|---|
| Example 3-1 | Treated by a 500-time diluted solution of Chemiclon G; Treated with TK-12 | $3.88 \times 10^3$ | 94.0 |
| Example 3-2 | Treated by a 500-time diluted solution of Chemiclon G; Treated with TK-151 | $7.45 \times 10^3$ | 87.0 |
| Example 3-3 | Treated by a 500-time diluted solution of Chemiclon G; Treated with TK-185 | $1.08 \times 10^3$ | 94.0 |
| Example 3-4 | Treated by a 500-time diluted solution of Chemiclon G; Treated with a composite of 3 bacterial strains | 25 | 88.5 |
| Comparative Example 3-1 | Treated by a 500-time diluted solution of Chemiclon G | $3.14 \times 10^4$ | 91.0 |
| Comparative Example 3-2 | Simultaneously treated by both a 500-time diluted solution of Chemiclon G and 3 bacterial strains | $1.02 \times 10^4$ | 90.5 |
| Comparative Example 3-3 | No treatment | $7.65 \times 10^4$ | 91.5 |

As shown in Table 4, seeds in Examples 3-1 to 3-4 which have been treated with antagonistic bacteria after treated by a 500-time diluted solution of Chemiclon G were each reduced in a contamination degree of *Xanthomonas campestris* p.v. *campestris* without impairing germination rates. Particularly, in seeds in Example 3-4 which were treated by a composite of antagonistic bacteria have substantially reduced in the contamination degree compared with seeds which have been treated by a single bacterial strain whereupon a very high controlling effect was observed therein. To the contrary, in Comparative Examples 3-2 in which seeds have been simultaneously treated by soaking them in the 500-time diluted solution of Chemiclon G and three bacterial strains, since the antagonistic bacteria were killed by the Chemiclon G, a similar effect to that of seeds which have been treated by the Chemiclon G only was merely able to be obtained.

Example 4

Suppressing Effect On Onset of *Xanthomonas campestris* p.v. *campestris* Against Seeds of Cabbage Using seeds in the above-described Examples 2-1 to 2-4 and Comparative Examples 2-1 and 2-4, seed sowing operations have been performed under two conditions, namely, under a natural condition and under a moistened condition by means of a tunnel cultivation. Then, each onset rate of diseases by *Xanthomonas campestris* p.v. *campestris* 2 weeks after the seed sowing operations was investigated. On this occasion, seed sowing tests using seeds in Examples 2-1 to 2-4 were named as Examples 4-1 to 4-4, respectively and seed sowing tests using seeds in Comparative Example 2-1 and 2-4 were named as Comparative Examples 4-1 and 4-4. Further, seeds were sown by 128 grains/area in each of nursing trays. The result is shown in Table 5.

TABLE 5

| Examples | Treatments | Onset rates of disease under a natural condition (%) | Onset rates of disease under a moistened condition (%) |
|---|---|---|---|
| Example 4-1 | Treated by a 500-time diluted solution of Chemiclon G; Treated with TK-12 | 12.5 | 36.0 |
| Example 4-2 | Treated by a 500-time diluted solution of Chemiclon G; Treated with TK-151 | 20.5 | 8.8 |
| Example 4-3 | Treated by a 500-time diluted solution of Chemiclon G; Treated with TK-185 | 11.8 | 18.6 |
| Example 4-4 | Treated by a 500-time diluted solution of Chemiclon G; Treated with a composite of 3 bacterial strains | 1.6 | 2.2 |
| Comparative Example 4-1 | Treated by a 500-time diluted solution of Chemiclon G | 37.0 | 52.6 |
| Comparative Example 4-2 | No treatment | 52.0 | 76.5 |

As shown in Table 5, in Examples 4-1 to 4-4 which used seeds that have been treated with antagonistic bacteria after having been sterilized by means of a chemical technique, onset rates of the disease caused by *Xanthomonas campestris* p.v. *campestris* were apparently suppressed as a whole. However, in Examples 4-1 to 4-3 thereamong which used seeds which have been treated by a single bacterial strain, fixing properties were reduced depending on nursing conditions whereupon there were some cases in which a suppressing effect was unable to be fully obtained. To the contrary, in Example 4-4 which used seeds which have been treated by a composite of bacterial strains, no or almost no detrimental effect on fixing properties to be derived from differences of nursing conditions was observed and a controlling effect in a consistent manner was observed whereupon it was clarified to control a secondary infection of the disease during a nursing period of time.

As described above, according to the present invention, seeds which have preliminarily been sterilized by at least one of the physical technique and chemical technique to reduce an amount of fungi or bacteria held by the seeds are treated by the effective microorganism which is antagonistic against the pathogen of the seed borne disease whereupon, while the seed borne disease can be efficiently controlled, germination of the seeds is not adversely affected thereby obtaining disease-free seeds of high quality having a low onset rate of diseases.

What is claimed is:

1. A method of controlling a seed disease comprising the steps of:
   sterilizing seeds by at least one of a physical technique and a chemical technique; and
   treating the thus sterilized seeds by an effective plurality of types of microorganisms which are antagonistic against a pathogen of a seed borne disease, wherein at least one type of said effective microorganisms is a bacterium belonging to the genus *Pantoea* and at least one other type of said effective microorganisms is a bacterium belonging to the genus *Leclercia*, each of said types of microorganisms belonging to the genus *Pantoea* and the genus *Leclercia* being antagonistic against a pathogenic bacterium belonging to the genus *Xanthomonas*.

2. The method of controlling the seed disease according to claim 1, wherein at least one type of said effective microorganisms is a microorganism separated from seeds which have been obtained by seed production.

3. The method of controlling the seed disease, according to claim 1, wherein the seeds to be treated are those which have been contaminated with the pathogen of the seed borne disease.

4. The method of controlling the seed disease according to claim 1, wherein the thus treated seeds are those belonging to a family selected from the group consisting of the family Brassicaceae, the family Umbelliferae, the family Solanaceae, the family Cucurbitaceae, the family Compositae, the family Liliaceae, the family Chenopodiaceae and the family Leguminosae.

5. The method of controlling the seed disease according to claim 1, wherein said physical technique is a dry-heating treatment or a warm-water treatment.

6. The method of controlling the seed disease according to claim 1, wherein said chemical technique is a treatment selected from the group consisting of a soaking treatment, a powder-coating treatment, and a coating-treatment, and wherein all three treatments are performed using a synthetic agrochemical.

7. The method of controlling the seed disease according to claim 1, wherein a treatment by said effective microorganisms is performed such that the seeds are soaked in an aqueous dispersion of the effective microorganisms.

8. The method of controlling the seed disease according to claim 1, wherein a treatment by said effective microorganisms is performed such that the seeds are pelleted by a coating material containing the effective microorganisms.

9. The method of controlling the seed disease according to claim 1, wherein a treatment by said effective microrganisms is performed such that the seeds are film-coated by a coating solution containing the effective microorganisms.

10. The method of controlling the seed disease according to claim 1, wherein a treatment by said effective microorganisms is performed such that the seeds are allowed to absorb water by contacting a carrier impregnated with an aqueous dispersion of the effective microorganisms.

11. Seeds a disease of which has been controlled by treating the seeds by the method of claim 1.

12. The method of controlling the seed disease according to claim 1, wherein *Pantoea* sp. TK-185 (FERM BP-7618) is used as one of said effective microorganisms.

13. The method of controlling the seed disease according to claim 1, wherein *Leclercia adecarboxylata* TK-151 (FERM BP-7617) is used as one of said effective microorganisms.

14. The method of controlling the seed disease according to claim 1, wherein said seed disease is a seed borne disease selected from the group consisting of *Alternaria Brassicae, Alternaria brassicicola, Peronospora brassicae, Pseudomonas syringae* p.v. *maculicola, Xanthomonas campestris* p.v. *campestris* and *Phoma lingam* of the cabbage, *Alternaria japonica, Alternaria brassicae, Fusarium oxysporum* f.sp. *raphani, Xanthomonas campestris* p.v. *campestris* of the radish, *Alternaria brassicae, Xanthomonas campestris* p.v. *campestris, Verticillium dahliae* of the Chinese cabbage, *Alternaria dauci, Alternaria radicina, Xanthomonas campestris* p.v. *carotae* of the carrot, *Septoria apii, Sclerotinia sclerotiorum, Pseudomonas syringae* p.v. *apii* of the celery, *Alternaria porri, Botrytis allii, Botrytis byssoidea, Fusarium oxysporum* f. sp. *cepae* and *Peronospora destructor* of the onion, *Peronospora farinosa, Fusarium oxysporum* f. sp *spinaciae, Colletotrichum dematium* of the spinach, *Alternaria solani, Clavibacter michiganensis* subsp. *michiganensis, Xanthomonas campestris* p.v. *vesicatoria* of the tomato, *Alternaria solani, Phomopsis vexans* of the egg plant, *Alternaria cucumerina, Pseudomonas syringae* p.v. *lachrymans, Xanthomonas campestris* p.v. *cucurbitae* of the cucumber, *Alternaria znniae, Xanthomonas campestris* p.v. *znniae* of the common zinnia, *Sclerotinia sclerotiorum, Alternaria helianti* of the sun flower, and *Xanthomonas campestris* p.v. *campestris* of the ornamental kale.

* * * * *